(12) United States Patent
Moriya et al.

(10) Patent No.: US 7,683,355 B2
(45) Date of Patent: Mar. 23, 2010

US007683355B2

(54) EXTREME ULTRA VIOLET LIGHT SOURCE APPARATUS

(75) Inventors: Masato Moriya, Hiratsuka (JP); Tamotsu Abe, Odawara (JP); Takashi Suganuma, Hiratsuka (JP); Hiroshi Someya, Hiratsuka (JP); Takayuki Yabu, Hiratsuka (JP); Akira Sumitani, Isehara (JP)

(73) Assignee: Komatsu Ltd., Tokyo (JP)

( * ) Notice: Subject to any disclaimer, the term of this patent is extended or adjusted under 35 U.S.C. 154(b) by 187 days.

(21) Appl. No.: 11/902,596

(22) Filed: Sep. 24, 2007

(65) Prior Publication Data

US 2008/0073598 A1 Mar. 27, 2008

(30) Foreign Application Priority Data

Sep. 27, 2006 (JP) ............................ 2006-263371

(51) Int. Cl.
*H05G 2/00* (2006.01)
*G21G 4/00* (2006.01)
*A61N 5/06* (2006.01)
*G01J 3/10* (2006.01)

(52) U.S. Cl. ............................ 250/504 R; 250/370.09; 250/365; 250/461.1; 378/119

(58) Field of Classification Search ............ 250/370.09, 250/365, 461.1, 493.1, 504 R; 378/119, 378/143
See application file for complete search history.

(56) References Cited

U.S. PATENT DOCUMENTS 6,232,613 B1 * 5/2001 Silfvast et al. .......... 250/504 R
6,437,283 B1 * 8/2002 Wiggermann et al. .... 219/121.7
6,834,069 B1 * 12/2004 Bergmann et al. ............ 372/57
7,372,056 B2 * 5/2008 Bykanov et al. ........ 250/504 R
7,439,530 B2 * 10/2008 Ershov et al. ........... 250/504 R
7,482,609 B2 * 1/2009 Ershov et al. ........... 250/504 R
7,589,337 B2 * 9/2009 Bykanov et al. ........ 250/504 R
2002/0063113 A1 * 5/2002 Wiggermann et al. .... 219/121.7
2005/0199829 A1 * 9/2005 Partlo et al. ............. 250/504 R
2006/0192152 A1 * 8/2006 Ershov et al. ............ 250/503.1
2007/0001131 A1 * 1/2007 Ershov et al. ............ 250/503.1
2007/0125970 A1 * 6/2007 Fomenkov et al. ...... 250/504 R
2007/0158596 A1 * 7/2007 Oliver et al. ............ 250/504 R
2008/0017801 A1 * 1/2008 Fomenkov et al. ....... 250/354.1
2008/0073598 A1 * 3/2008 Moriya et al. ........... 250/504 R

FOREIGN PATENT DOCUMENTS

JP 2003-229298 8/2003

* cited by examiner

*Primary Examiner*—Bernard E Souw
(74) *Attorney, Agent, or Firm*—Wenderoth, Lind & Ponack, L.L.P.

(57) ABSTRACT

An EUV light source apparatus capable of preventing the efficiency of generation of EUV light from decreasing due to deterioration of a window of an EUV light generation chamber. The EUV light source apparatus includes an EUV light generation chamber provided with a window, a driver laser which generates a laser beam, a concave lens which enlarges the laser beam, a convex lens which collimates the enlarged laser beam, a parabolic concave mirror which is arranged in the EUV light generation chamber and reflects the collimated laser beam to collect the laser beam to a target material, a parabolic concave mirror adjusting mechanism which adjusts position and angle of the parabolic concave mirror, an EUV light collector mirror which collects EUV light, and a purge gas supply unit which supplies a purge gas for protecting the window and the parabolic concave mirror.

9 Claims, 10 Drawing Sheets

(a)

(b)

EXTREME ULTRA VIOLET LIGHT SOURCE APPARATUS

BACKGROUND OF THE INVENTION

1. Field of the Invention

The present invention relates to an LPP (laser produced plasma) type EUV (extreme ultra violet) light source apparatus that generates extreme ultra violet light to be used for exposing a semiconductor wafer or the like.

2. Description of a Related Art

Recently, as semiconductor processes become finer, photolithography has been making rapid progress toward a higher resolution, and for the next generation, micro-fabrication of 100 nm to 700 nm, and further, micro-fabrication of 50 nm or less is being required. Accordingly, in order to meet the requirement of micro-fabrication of 50 nm or less, for example, exposure equipment is expected to be developed by combining an EUV light source generating extreme ultra violet light with a wavelength of approximately 13 nm and reduced projection reflective optics.

The EUV light sources include three kinds, namely, an LPP (laser produced plasma) light source using plasma generated by irradiating a target with a laser beam, a DPP (discharge produced plasma) light source using plasma generated by electric discharge, and an SR (synchrotron radiation) light source using orbital radiation light. Among these, the LPP light source is considered to be most promising as a light source for EUV lithography for which power of tens of watts or more is required. This is because the LLP light source has the advantages that an extremely high luminance close to black body radiation can be obtained because plasma density can be increased considerably, that light emission only in the necessary wavelength band is possible by selecting a target material, that an extremely large collection solid angle as large as 2π sterad can be ensured because of a point light source having almost an isotropic angle distribution and no structure around the light source such as an electrode, and so on.

FIG. 10 is a diagram showing an outline of a conventional LPP type EUV light source apparatus. As shown in FIG. 10, the EUV light source apparatus includes a driver laser 101, an EUV light generation chamber 102, a target material supply unit 103, and a laser beam collecting optics 104.

The driver laser 101 is an oscillation-amplification type laser apparatus that generates a driving laser beam to be used to excite a target material.

The EUV light generation chamber 102 is a chamber in which EUV light is generated and is evacuated by a vacuum pump 105 in order to facilitate turning the target material into plasma and prevent EUV light from being absorbed. In the EUV light generation chamber 102, a window 106 is attached, which causes a laser beam 120 generated by the driver laser 101 to pass through the inside of the EUV light generation chamber 102. Further, within the EUV light generation chamber 102, a target ejection nozzle 103*a*, a target collection tube 107, and an EUV light collector mirror 108 are arranged.

The target material supply unit 103 supplies a target material to be used to generate EUV light into the EUV light generation chamber 102 via the target ejection nozzle 103*a*, which is part of the target material supply unit 103. Among the supplied target materials, those not irradiated with a laser beam and no longer necessary are collected by the target collection tube 107.

The laser beam collecting optics 104 includes a mirror 104*a* that reflects the laser beam 120 output from the driver laser 101 toward the EUV light generation chamber 102, a mirror adjusting mechanism 104*b* that adjusts the position and angle (tilt angle) of the mirror 104*a*, a collecting device 104*c* that collects the laser beam 120 reflected by the mirror 104*a*, and a collecting device adjusting mechanism 104*d* that moves the collecting device 104*c* along the optical axis of the laser beam. The laser beam 120 collected by the laser beam collecting optics 104 passes through the window 106 and a hole formed in the center of the EUV light collector mirror 108 and reaches the orbit of the target material. In this manner, the laser beam collecting optics 104 collects the laser beam 120 so as to form its focus on the orbit of the target material. Due to this, the target material 109 is excited and turned into plasma and the EUV light is generated.

The EUV light collector mirror 108 is, for example, a concave mirror, on the surface of which a Mo/Si film that reflects light with a wavelength of 13.5 nm with a high reflectance is formed, and reflects generated EUV light 121 to thereby collect the light to IF (intermediate focusing point). The EUV light 121 reflected by the EUV light collector mirror 108 passes through a gate valve 110 provided in the EUV light generation chamber 102 and a filter 111 that removes unnecessary light (electromagnetic wave or light with a wavelength shorter than that of the EUV light, light with a wavelength longer than that of the EUV light, for example, ultra violet light, visible beam, infrared light, etc.) from among the light generated from the plasma and causes only the desired EUV light (for example, light with a wavelength of 13.5 nm) to be transmitted. The EUV light 121 collected to the IF (intermediate focusing point) is then guided to exposure equipment or the like via transmission optics.

Since a large amount of energy is radiated from the plasma generated in the EUV light generation chamber 102, the temperature of the parts in the EUV light generation chamber 102 is raised due to this radiation. Some techniques to prevent such a rise in temperature of parts are known.

As a related art, in Japanese Patent Application Publication JP-P2003-229298A, an X-ray generation apparatus is described, which comprises an X-ray source that turns a target material into plasma and radiates X-rays from the plasma, and a vacuum container that contains the X-ray source, and which is characterized in that an inner wall formed by a material having a high absorptance against the electromagnetic wave in the range from infrared to X-ray is provided on the inner side of the vacuum container. According to the X-ray generation apparatus, it is possible to prevent the parts within the vacuum container from being heated unnecessarily due to the radiation energy reflected and scattered by the inner wall of the vacuum container.

By the way, the plasma generated in the EUV light generation chamber 102 shown in FIG. 10 diffuses as time elapses and part of it scatters as atoms or ions. The inner wall and the structures of the EUV light generation chamber 102 are irradiated with the atoms or ions.

Due to the irradiation with the atoms scattered from the above-mentioned plasma, the following phenomenon may occur.

(1) The atoms scattered from the plasma stick to the surface of the window 106 at the inner side of the EUV light generation chamber 102. The atoms having thus stuck to the surface of the window 106 at the inner side of the EUV light generation chamber 102 absorb the laser beam 120.

Due to the irradiation with the ions scattered from the above-mentioned plasma, the following phenomena may occur.

(2) The surface of the window 106 at the inner side of the EUV light generation chamber 102 is irradiated with the ions scattered from the plasma and the surface of the window 106 at the inner side of the EUV light generation chamber 102 may deteriorate (the surface becomes coarse and unsmoothed). Due to this, the window 106 absorbs the laser beam 120 output from the driver laser 101.

(3) The inner wall and the structures of the EUV light generation chamber 102 are irradiated with the ions scattered from the plasma. Due to this sputtering, the atoms scattered from the inner wall and the structures of the EUV light generation chamber 102 stick to the surface of the window 106 at the inner side of the EUV light generation chamber 102. In this manner, the atoms having stuck to the surface of the window 106 at the inner side of the EUV light generation chamber 102 absorb the laser beam 120.

(4) Since the window 106 absorbs short-wavelength electromagnetic waves (light) generated from the plasma, the material thereof deteriorates. Due to this, the window 106 absorbs the laser 120.

If the above-mentioned phenomena (1) to (4) occur, the energy to turn the target material into plasma is lowered and the efficiency of generation of the EUV light 121 is decreased.

In addition, if the window 106 or the atoms having stuck to the window 106 absorb the laser beam 120, the temperature of the window 106 rises and distortion occurs in the window 106, and the ability to collect light decreases. Such a decrease in the ability to collect light causes a further decrease in the efficiency of generation of the EUV light 121. Furthermore, if the distortion of the window 106 becomes larger, it may eventually lead to damage of the window 106.

There may be a case where part of the laser beam collecting optics 104 (for example, lens, mirror, etc.) is arranged within the EUV light generation chamber 102. In such a case, also at the part of the laser beam collecting optics 104 arranged within the EUV light generation chamber 102, the phenomena in the above-mentioned (1) to (4) may occur. In particular, when a mirror that reflects the laser beam is arranged within the EUV light generation chamber 102, if the phenomena in the above-mentioned (1) to (4) occur, the reflectance of the laser beam of the enhanced reflection coating of the mirror reflecting surface decreases. Due to this, the energy to turn the target material into plasma is lowered and the efficiency of generation of the EUV light 121 decreases.

In general, in the field of optics, it is known that the shorter the focal length, the smaller the image is, and the longer the focal length, the larger the image is. Taking this into account, it is preferable to reduce the light collection size (spot size) of the laser beam 120 by reducing the focal length of the laser beam collecting optics 104 in order to improve the efficiency of generation of the EUV light 121. However, in order to reduce the focal length of the laser beam collecting optics 104, it is necessary to reduce the distance between the window 106 and the plasma. Because of this, it becomes more likely that the phenomena in (1) to (4) described above occur on the surface of the window 106 at the inner side of the EUV light generation chamber 102.

In addition, as mentioned above, in order to increase the transmittance of the EUV light 121 generated from the plasma, it is necessary to maintain the inside of the EUV light generation chamber 102 at substantially vacuum by the vacuum pump 105. Because of this, the heat at the surface of the window 106 at the inner side of the EUV light generation chamber 102 or at part of the laser beam collecting optics 104 arranged inside the EUV light generation chamber 102 is difficult to diffuse and the deterioration of the devices will proceed.

SUMMARY OF THE INVENTION

The present invention has been developed with these problems being taken into account. An object of the present invention is to provide an extreme ultra violet light source apparatus capable of preventing the reduction in the efficiency of generation of the EUV light due to the deterioration of the window of the EUV light generation chamber.

In order to attain the above-mentioned object, an extreme ultra violet light source apparatus according to an aspect of the present invention is an extreme ultra violet light source apparatus which generates extreme ultra violet light by irradiating a target material with a laser beam and thereby turning the target material into plasma, and the apparatus comprises: an extreme ultra violet light generation chamber in which extreme ultra violet light is generated; a target material supply unit which supplies a target material into the extreme ultra violet light generation chamber; a driver laser which generates a laser beam; a window which is provided in the extreme ultra violet light generation chamber and allows the laser beam to be transmitted into the extreme ultra violet light generation chamber; a laser beam collecting optics which collects the laser beam generated by the driver laser to a target material supplied into the extreme ultra violet light generation chamber so as to generate plasma; an extreme ultra violet light collecting optics which collects the extreme ultra violet light generated from the plasma to output the extreme ultra violet light; and a purge gas supply unit which supplies a purge gas for protecting a surface of the window at an inner side of the extreme ultra violet light generation chamber and/or an optical surface of at least one optical device which is included in the laser beam collecting optics and arranged in the extreme ultra violet light generation chamber.

According to the present invention, it is possible to prevent the window of the EUV light generation chamber and/or the laser beam collecting optics from deteriorating and to prevent the efficiency of generation of EUV light from decreasing.

DESCRIPTION OF THE PREFERRED EMBODIMENTS

Figure 1:
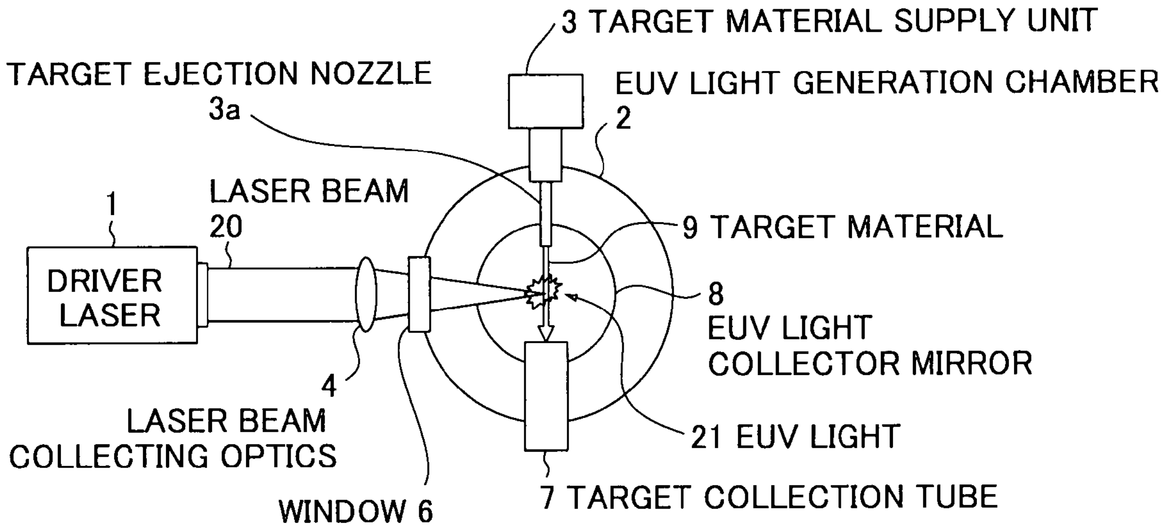
FIG. 1 is a schematic diagram showing an outline of an EUV light source apparatus according to the present invention.

Embodiments of the present invention will be described below in detail with reference to drawings. The same components are assigned the same reference numerals and their explanation is omitted.

FIG. 1 is a schematic diagram showing an outline of an extreme ultra violet light source apparatus (hereinafter, also referred to simply as an "EUV light source apparatus") according to the present invention. As shown in FIG. 1, the EUV light source apparatus includes a drive laser 1, an EUV light generation chamber 2, a target material supply unit 3, and a laser beam collecting optics 4.

The driver laser 1 is an oscillation-amplification type laser apparatus that generates a driving laser beam to be used to excite a target material. As the driver laser 1, various publicly known lasers (for example, ultra violet light laser such as KrF laser, XeF laser, etc., or infrared laser such as Ar laser, $CO_2$ laser, YAG laser, etc.) can be used.

The EUV generation chamber 2 is a vacuum chamber in which EUV light is generated. In the EUV light generation chamber 2, a window 6 that allows a laser beam 20 generated by the driver laser 1 to pass through the inside of the EUV light generation chamber 2 is attached. Further, inside the EUV light generation chamber 2, a target ejection nozzle 3*a*, a target collection tube 7, and an EUV light collector mirror 8 are arranged.

The target material supply unit 3 supplies a target material to be used to generate EUV light into the EUV light generation chamber 2 via the target ejection nozzle 3*a*, which is a part of the target material supply unit 3. Among the supplied target materials, those not irradiated with a laser beam and no longer necessary are collected by the target collection tube 7. As a target material, various known materials (for example, tin (Sn), xenon (Xe), etc.) can be used. In addition, the state of the target material may be solid, liquid, or gas, and may be supplied to the space in the EUV light generation chamber 2 in various known states, such as a state of continuous flow (target ejection flow), a state of liquid drop (droplet), etc. For example, when a liquid xenon (Xe) is used as a target material, the target material supply unit 3 includes a gas tank for supplying a highly pure xenon gas, amass flow controller, a cooling device for liquefying the xenon gas, a target ejection nozzle, etc. In addition, when a droplet is generated, a vibrating device such as a piezo element etc. is added to the configuration including them.

The laser beam collecting optics 4 collects the laser beam output from the driver laser 1 so as to form the focus on an orbit of the target material. Thereby, the target material 9 is excited and turned into plasma, and the EUV light 21 is generated. The laser beam collecting optics 4 may be configured of one optical device (for example, a convex lens) or a plurality of optical devices. When the laser beam collecting optics 4 is configured of a plurality of optical devices, some of them may be arranged in the EUV light generation chamber 2.

The EUV light collector mirror 8 is, for example, a concave mirror, on the surface of which a Mo/Si film that reflects light of a wavelength of 13.5 nm with a high reflectance is formed, and reflects the generated EUV light 21 to collect and guide the EUV light to transmission optics. Further, the EUV light 21 is guided to exposure equipment, etc. via the transmission optics. In FIG. 1, the EUV light collector mirror 8 collects the EUV light 21 toward a direction of this side of the drawing.

Next, an EUV light source apparatus according to a first embodiment of the present invention will be described.

Figure 2:
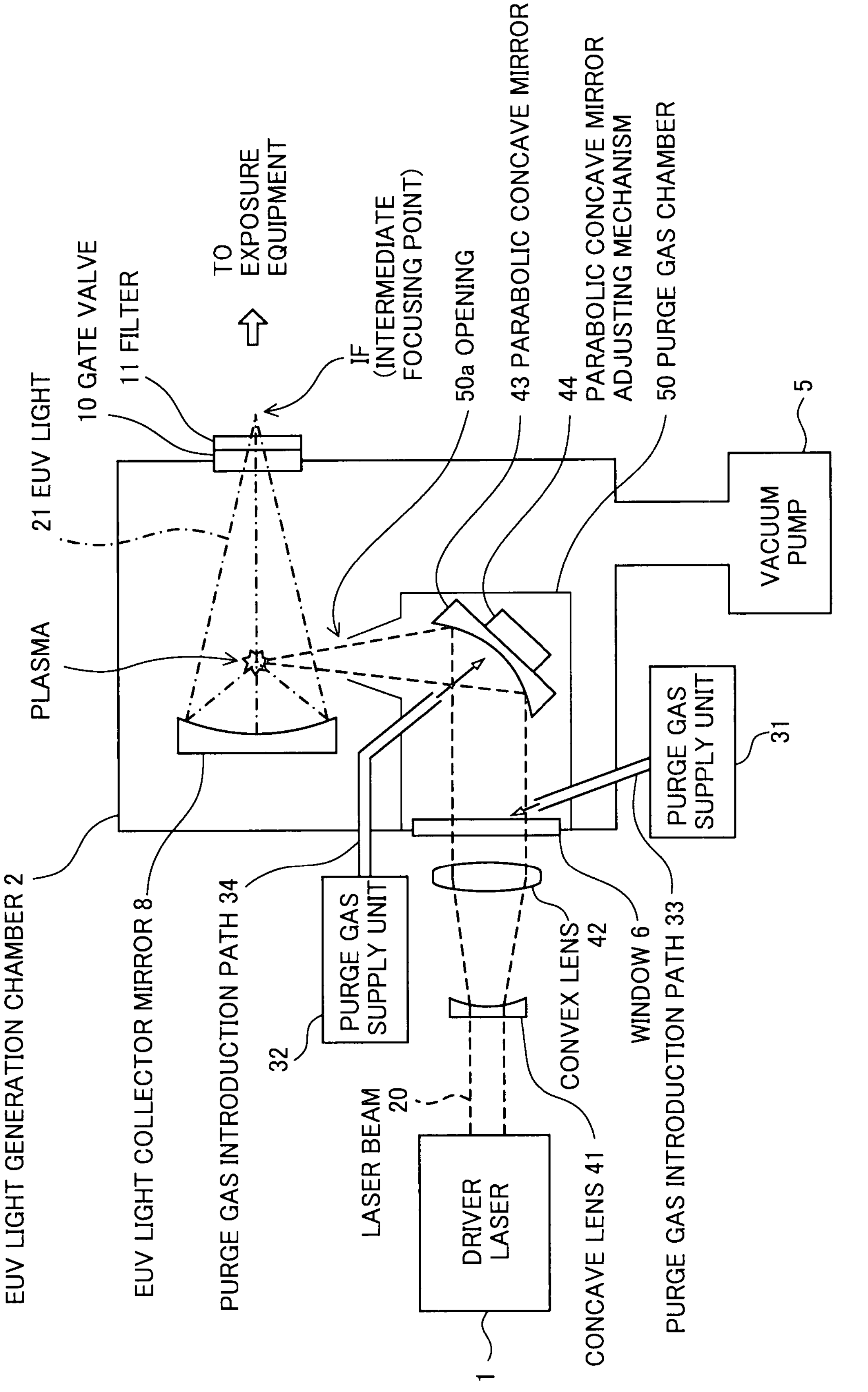
FIG. 2 is a schematic diagram showing an EUV light source according to a first embodiment of the present invention.

FIG. 2 is a schematic diagram showing the EUV light source apparatus according to the present embodiment. In FIG. 2, the target material supply unit 3 and the target material collection tube 7 (refer to FIG. 1) are not shown schematically, and it is assumed that the target material is ejected in the vertical direction to the drawing.

As shown in FIG. 2, a laser beam 20 emitted from the driver laser 1 in the rightward direction in the drawing is enlarged by a concave lens 41, collimated by a convex lens 42, transmitted through the window 6, and input into the EUV light generation chamber 2. As the material of the concave lens 41, the convex lens 42, and the window 6, those which absorb the laser beam 20 little, such as synthetic quartz, $CaF_2$, $MgF_2$, etc., are preferable. When an infrared laser such as $CO_2$ laser, etc. is used as the driver laser 1, ZnSe, GaAs, Ge, Si, etc. are suitable for the material of the concave lens 41, the convex lens 42, and the window 6. It is preferable to apply anti-reflection coating of dielectric multilayer film to the surface of the concave lens 41, the convex lens 42, and the window 6.

In the EUV light generation chamber 2, a parabolic concave mirror 43 and a parabolic concave mirror adjusting mechanism 44 that adjusts the position and angle (tilt angle) of the parabolic concave mirror 43 are arranged. As the substrate material of the parabolic concave mirror 43, synthetic quartz, Ca $F_2$, Si, Zerodur®, Al, Cu, Mo, etc., can be used and it is preferable to apply anti-reflection (AR) coating of dielectric multilayer film to the surface of such a substrate.

Figure 3:
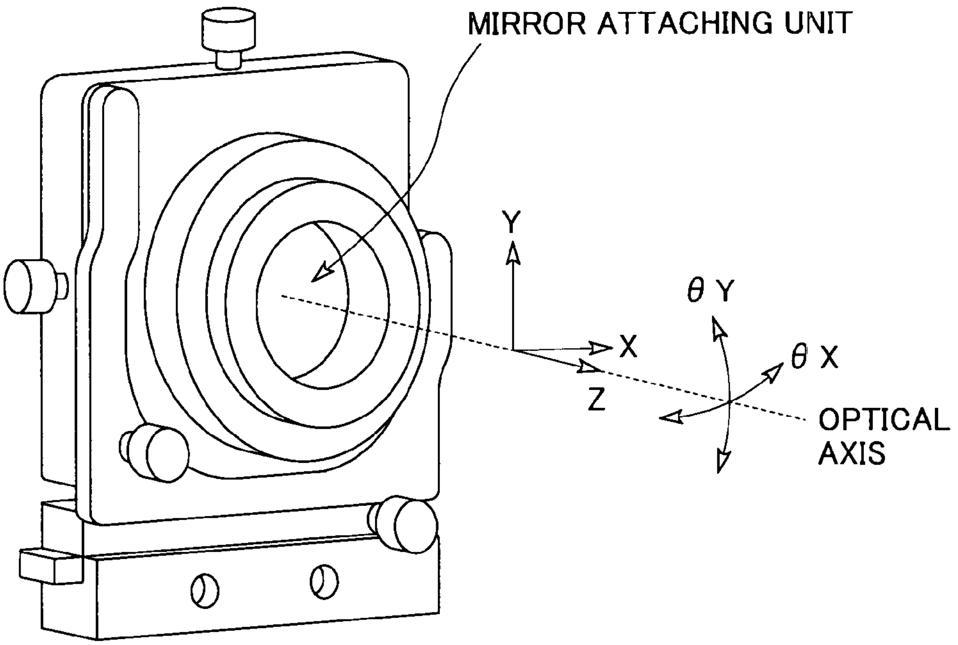
FIG. 3 is a schematic diagram showing an example of a parabolic concave mirror adjusting mechanism in FIG. 2.
Figure 3:
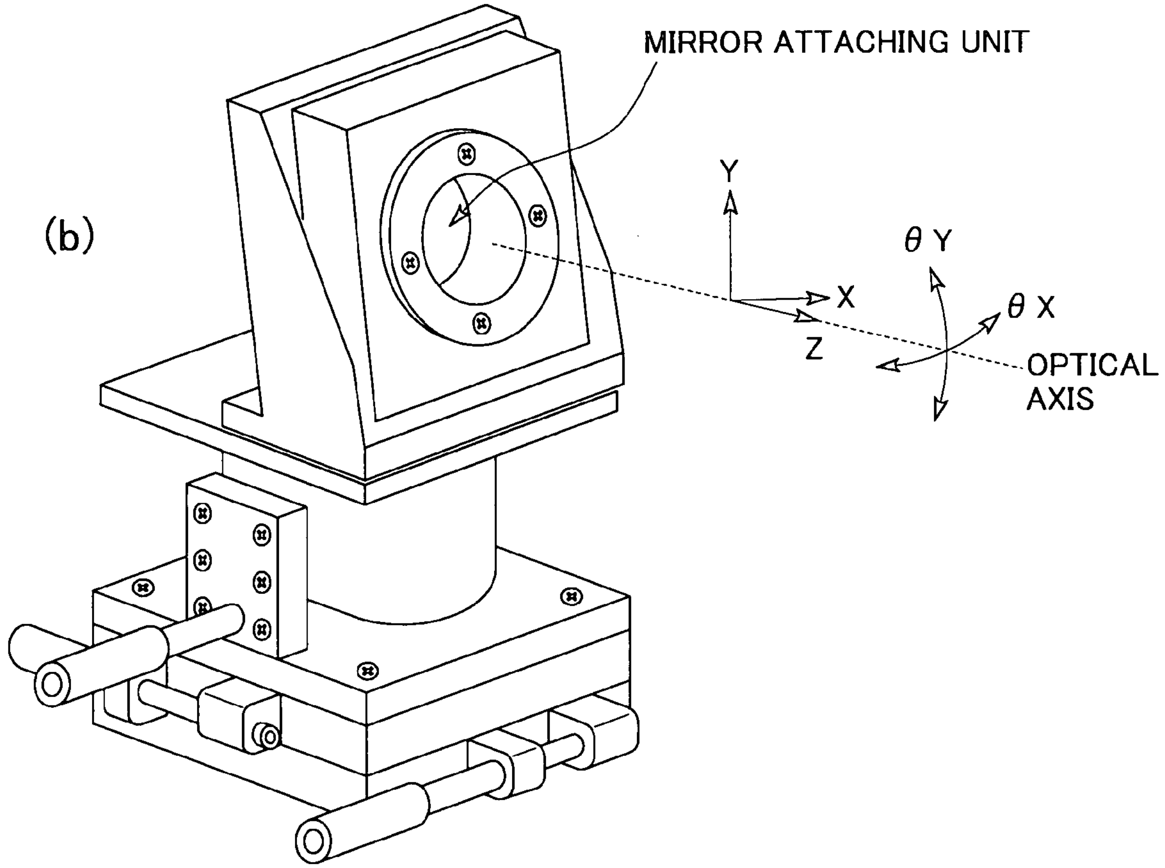

FIG. 3 is a diagram showing an example of the parabolic concave mirror adjusting mechanism 44. As shown in FIG. 3, it is preferable for the parabolic concave mirror adjusting mechanism 44 to be capable of moving the parabolic concave mirror 43 in the x-axis direction, y-axis direction, and z-axis direction while maintaining the tilt angle of the parabolic concave mirror 43 as well as adjusting the tilt angle in the θx direction and θy direction of the parabolic concave mirror 43 in order to adjust the angle of the optical axis of the laser beam.

Referring to FIG. 2 again, the laser beam 20 transmitted through the window 6 and input into the EUV light generation chamber 2 is reflected upward in the drawing by the parabolic concave mirror 43 and collected onto the orbit of the target material. Due to this, the target material is excited and turned into plasma, and thus the EUV light 21 is generated.

By enlarging the input light and then collecting the light as described above, it is possible to make a length of a back focus of the laser beam collecting optics 4 longer than the focal length of an optical device arranged at a light output side, that is, the parabolic concave mirror 43. Such optics is called Retrofocus™.

The EUV light collector mirror 8 is, for example, a concave mirror, on the surface of which a Mo/Si film that reflects light with a wavelength of 13.5 nm with a high reflectance is formed, and reflects the generated EUV light 21 in the rightward direction in the drawing to collect the EUV light 21 to the IF (intermediate focusing point). The EUV light 21 reflected by the EUV light collector mirror 8 passes through a gate valve 10 provided in the EUV light generation chamber 2 and a filter 11 that removes unnecessary light (electromagnetic wave or light with a wavelength shorter than that of the EUV light, light with a wavelength longer than that of the EUV light, for example, ultra violet light, visible beam, infrared light, etc.) from among the light generated from the plasma and causes only the desired EUV light, for example, light with a wavelength of 13.5 nm to be transmitted. The EUV light 21 collected to the IF (intermediate focusing point) is then guided to exposure equipment or the like via a transmission optics.

The EUV light source apparatus further includes purge gas supply units 31 and 32 each supplies a purge gas by ejecting the purge gas, a purge gas introduction path 33 that guides the purge gas ejected from the purge gas supply unit 31 to the surface of the window 6 at the inner side of the EUV light generation chamber 2, and a purge gas introduction path 34 that guides the purge gas ejected from the purge gas supply unit 32 to the reflecting surface of the parabolic concave mirror 43. As a purge gas, inactive gas, for example, Ar, He, $N_2$, Kr, etc. is preferable.

Further, to the inner wall of the EUV light generation chamber 2, a purge gas chamber 50 is attached that surrounds the window 6, the parabolic concave mirror 43, and the parabolic concave mirror adjusting mechanism 44. The upper part of the purge gas chamber 50 in the drawing is tapered cylinder-shaped and at the top end thereof (upper part in the drawing), an opening 50*a* is provided, which allows the laser beam 20 reflected by the parabolic concave mirror 43 to pass through.

According to the present embodiment, the purge gas is sprayed to the surface of the window 6 at the inner side of the EUV light generation chamber 2 and the reflecting surface of the parabolic concave mirror 43. Since the purge gas shuts out the atoms and ions scattered from the plasma, it is possible to prevent the atoms and ions scattered from the plasma from reaching the surface of the window 6 at the inner side of the EUV light generation chamber 2 and the reflecting surface of the parabolic concave mirror 43. Due to this, it is possible to prevent the window 6 and the parabolic concave mirror 43 from deteriorating and the efficiency of generation of the EUV light 21 from decreasing. Ar has properties of absorbing electromagnetic wave (light) with a wavelength shorter than that of the EUV light 21. Because of this, in the case where Ar is used as a purge gas, it is possible to more effectively prevent the window 6 and the parabolic concave mirror 43 from deteriorating due to the electromagnetic wave (light) with a short wavelength generated from the plasma.

When the temperatures of the window 6 and the parabolic concave mirror 43 rise, the heat is conducted to the purge gas. Because of this, it is possible to prevent the window 6 and the parabolic concave mirror 43 from deteriorating due to heat and the efficiency of generation of the EUV light 21 from decreasing. Since the heated purge gas is suctioned by the vacuum pump 5 via the opening 50*a* of the purge gas chamber 50, it is unlikely that the temperature of the purge gas in the purge gas chamber 50 rises unlimitedly.

As described above, the purge gas ejected from the purge gas introduction paths 33 and 34 is suctioned by the vacuum pump 5. However, by providing the purge gas chamber 50, it is possible to maintain to some extent the density of the purge gas around the surface of the window 6 at the inner side of the EUV light generation chamber 2 and the parabolic concave mirror 43. Due to this, it is possible to more effectively prevent the window 6 and the parabolic concave mirror 43 from deteriorating. Further, with the ions scattered from the plasma, the inner wall and the structures of the EUV light generation chamber 2 are irradiated, and the atoms scattered from the inner wall and the structures by sputtering are shut out by the purge gas chamber 50. Therefore, it is possible to prevent the atoms scattered by sputtering from sticking to the surface of the window 6 at the inner side of the EUV light generation chamber 2 and the parabolic concave mirror 43. In addition, since the surface of the window 6 at the inner side of the EUV light generation chamber 2 does not face the plasma directly, it is unlikely that the surface is irradiated with the atoms and ions scattered from the plasma and it is possible to more effectively prevent the window 6 from deteriorating.

By enlarging the laser beam 20 by the concave lens 41, collimating the laser beam 20 by the convex lens 42, and collecting the laser beam 20 by the parabolic concave mirror 43, it is possible to increase the distance between the plasma and the parabolic concave mirror 43 and the distance between the plasma and the window 6. As described above, by increasing the distance between the plasma and the parabolic concave mirror 43 and the distance between the plasma and the window 6, it is possible to reduce the density of the atoms and ions that fly from the plasma to the parabolic concave mirror 43 and the density of the electromagnetic wave (light) with a short wavelength that reaches the parabolic concave mirror 43 from the plasma. Due to this, while maintaining the energy density of the laser beam 20 to generate plasma by reducing the size (spot size) of the laser beam 20, it is possible to prevent the reflecting surface of the parabolic concave mirror 43 from being sputtered by the ions that fly from the plasma, prevent the atoms that fly from the plasma from sticking to the reflecting surface of the parabolic concave mirror 43, and prevent the parabolic concave mirror 43 from deteriorating by absorbing the electromagnetic wave (light) with a short wavelength generated from the plasma.

Further, by enlarging the laser beam 20 by the concave lens 41 and collimating the laser beam 20 by the convex lens 42, it is possible to reduce the energy density of the laser beam 20 input to the window 6. Due to this, even if the window 6 deteriorates to some degree, it is possible to suppress the temperature of the laser beam 20 from rising and prevent the window 6 from breaking. In FIG. 2, although the window 6 is attached such that it is substantially perpendicular to the optical axis of the laser beam 20, the window 6 may be attached to be tilted with respect to the optical axis of the laser beam 20 so as to reduce the energy density of the laser beam 20 input to the window 6.

Figure 4:
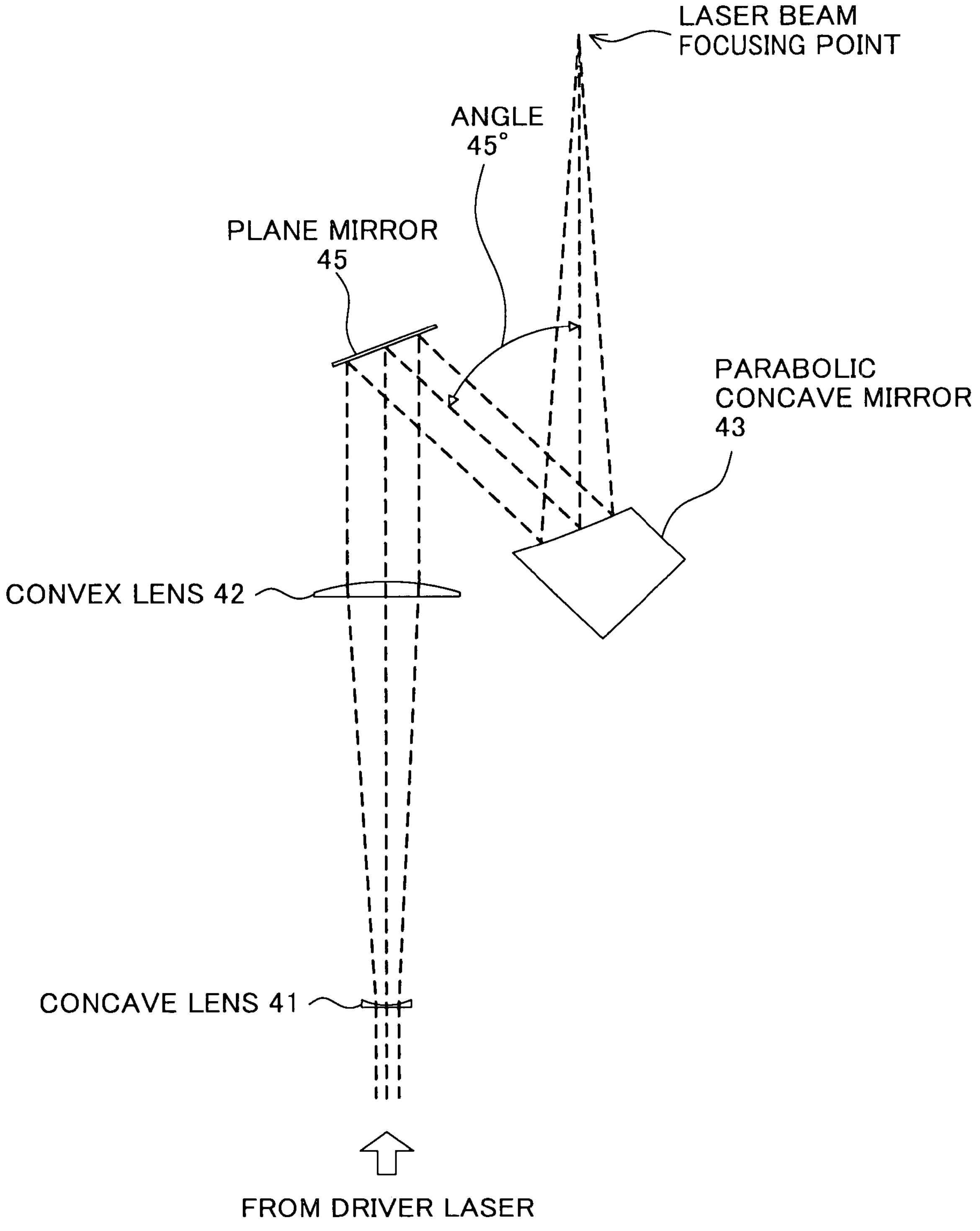
FIG. 4 is a schematic diagram showing a variation of a laser beam collecting optics in FIG. 2.

In the present embodiment, the laser beam 20 collimated by the convex lens 42 enters the parabolic concave mirror 43, however, a plane mirror 45 may be further provided that reflects the laser beam collimated by the convex lens 42 toward the parabolic concave mirror 43 in the light path between the convex lens 42 and the parabolic concave mirror 43, as shown in FIG. 4. In this case, it is preferable to set the angle between the optical axis of the laser beam input to the parabolic concave mirror 43 from the plane mirror 45 and the optical axis of the laser beam reflected and collected by the parabolic concave mirror 43 to substantially 45 degrees. In general, in the case of a parabolic concave mirror, in the case where the incidence angle of light when designing an optics (designed value) is different from the incidence angle of light when used after actually manufactured (actual value), the coma-aberration increases and the collection performance is degraded. However, by setting the angle between the optical axis of the laser beam input to the parabolic concave mirror 43 and the optical axis of the laser beam reflected and collected by the parabolic concave mirror 43 to substantially 45 degrees, it is possible to suppress the increase in coma-aberration to a relatively small amount in the case where the angle of light input to the parabolic concave mirror 43 (actual value) is different from the incidence angle of light when designing the optics (designed value).

In order to adjust the alignment (position and tilt angle) of the parabolic concave mirror 43 close to the designed value, it is preferable to manufacture the concave lens 41, the convex lens 42, the window 6, and the parabolic concave mirror 43 integrally into one unit and finish the alignment of the parabolic concave mirror 43 before the unit is incorporated in the EUV light generation chamber 2, such that the designed laser beam collection performance can be obtained.

In addition, in the present embodiment, two lenses (the concave lens 41 and the convex lens 42) are used, however, three or more lenses may be used.

Next, an EUV light source apparatus according to a second embodiment will be described.

Figure 5:
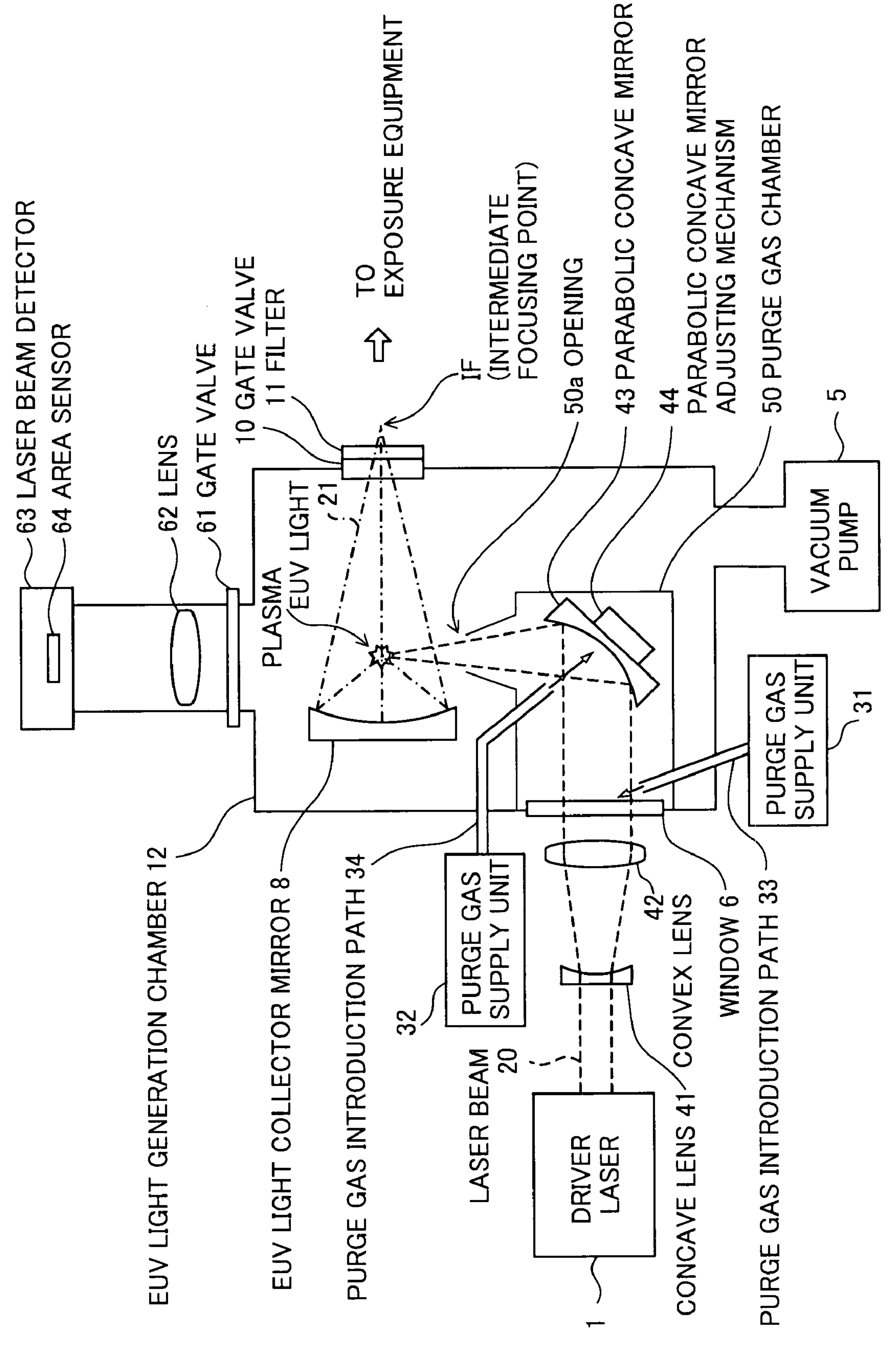
FIG. 5 is a schematic diagram showing an EUV light source apparatus according to a second embodiment of the present invention when emitting EUV light.
Figure 6:
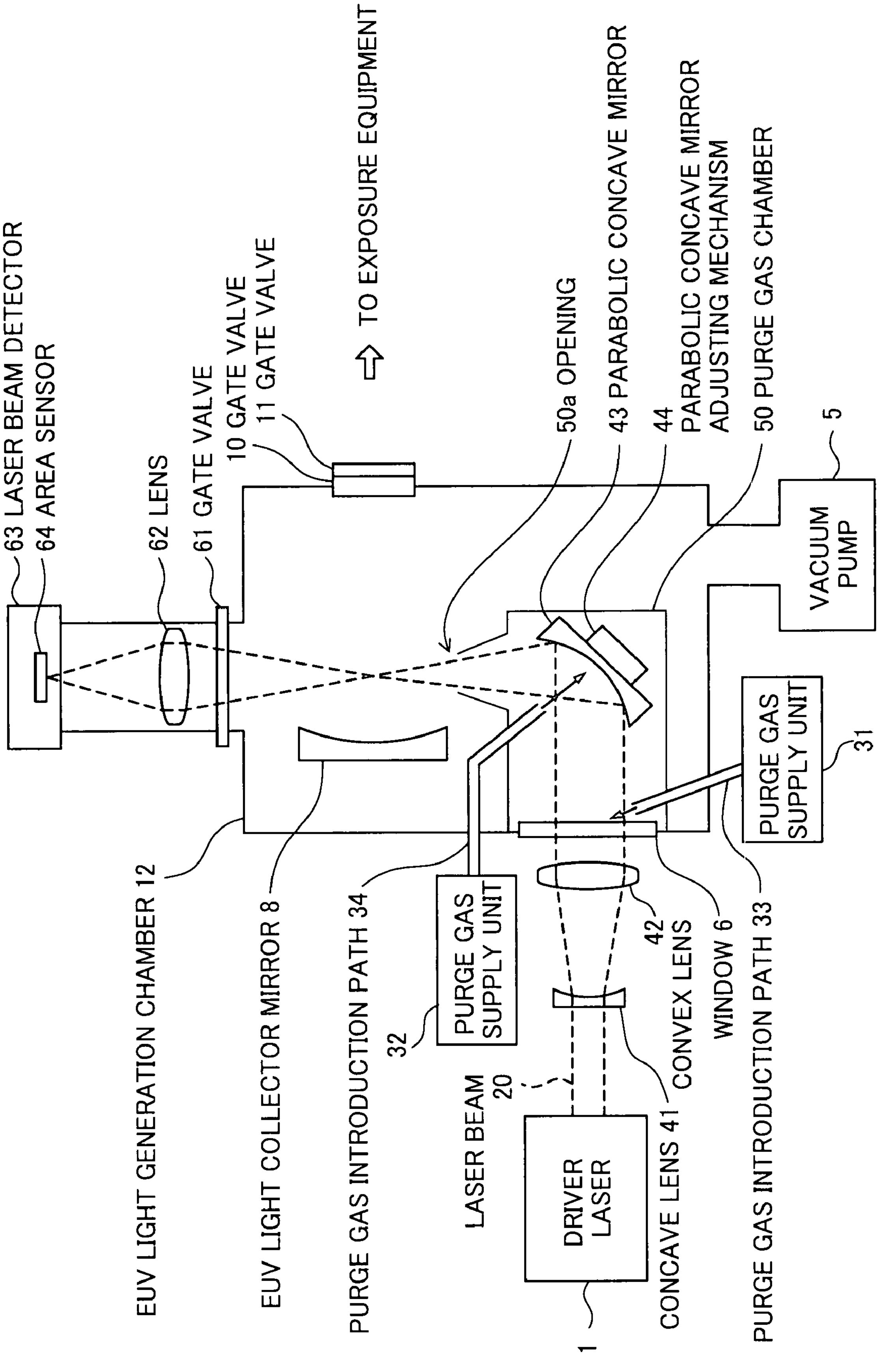
FIG. 6 is a schematic diagram showing the EUV light source apparatus according to the second embodiment of the present invention when a parabolic concave mirror is aligned.

FIGS. 5 and 6 are schematic diagrams showing the EUV light source apparatus according to the present embodiment. In FIGS. 5 and 6, the target material supply unit 3 and the target material collection tube 7 (refer to FIG. 1) are not shown schematically, and it is assumed that the target material is ejected vertically to the drawing.

As shown in FIGS. 5 and 6, the EUV light source apparatus further includes a gate valve 61, a lens 62, and a laser beam detector 63, in addition to the EUV light source apparatus according to the first embodiment described above. The laser beam detector 63 includes an area sensor 64.

FIG. 5 is a schematic diagram showing the EUV light source apparatus according to the present embodiment when emitting the EUV light, and FIG. 6 is a schematic diagram showing the EUV light source apparatus according to the present embodiment when the parabolic concave mirror is aligned.

As shown in FIG. 5, when the EUV light is generated, the gate valve 61 is closed. Due to this, it is possible to protect the lens 62 and the laser beam detector 63.

On the other hand, as shown in FIG. 6, when the parabolic concave mirror 43 is aligned, the ejection of the target material is stopped and the gate valve 61 is opened. Due to this, the laser beam 20 reflected by the parabolic concave mirror 43 passes through the gate valve 61 and is collected on the area sensor 64 by the lens 62, and the image is formed. By photographing the image by the area sensor 64, it is possible to obtain information about the position, at which the laser beam 20 is collected, and the shape of the collected light spot. Based on the information, it is possible to carry out alignment of the parabolic concave mirror 43 by adjusting the parabolic concave mirror adjusting mechanism 44.

Next, an EUV light source apparatus according to a third embodiment of the present invention will be described.

Figure 7:
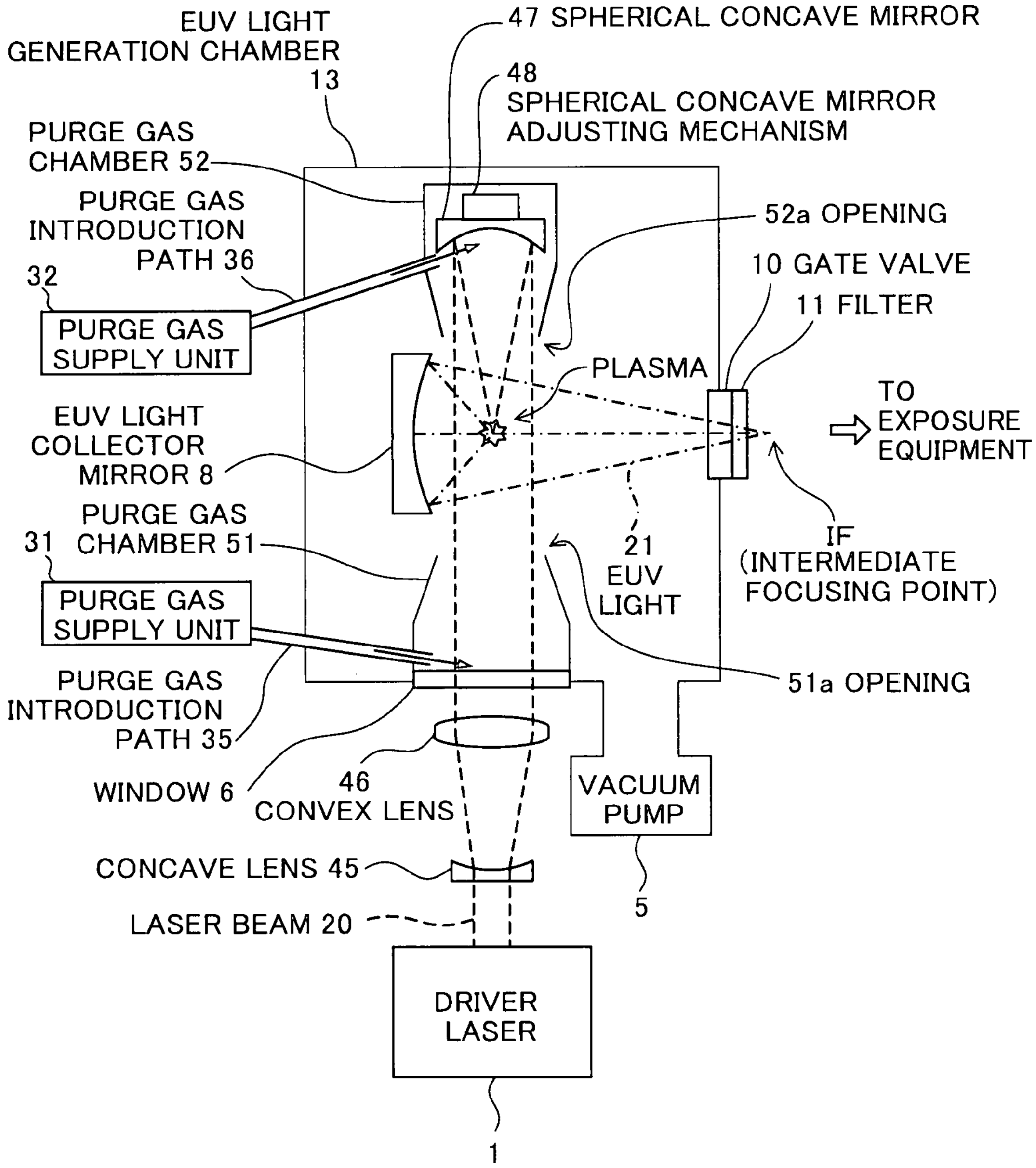
FIG. 7 is a schematic diagram showing an EUV light source apparatus according to a third embodiment of the present invention.

FIG. 7 is a schematic diagram showing the EUV light source apparatus according to the present embodiment. In FIG. 7, the target material supply unit 3 and the target material collection tube 7 (refer to FIG. 1) are not shown schematically, and it is assumed that the target material is ejected vertically to the drawing.

As shown in FIG. 7, the laser beam 20 emitted upward in the drawing from the driver laser 1 is enlarged by the concave lens 45, collimated by a convex lens 46, transmitted through the window 6, and input into an EUV light generation chamber 13.

In the EUV light generation chamber 13, a spherical concave mirror 47 and a spherical concave mirror adjusting mechanism 48 that adjusts the position and angle (tilt angle) of the spherical concave mirror 47 are arranged.

The laser beam 20 having been transmitted through the window 6 and input into the EUV light generation chamber 13 is reflected downward in the drawing by the spherical concave mirror 47 and collected on an orbit of the target material. Due to this, the target material is excited and turned into plasma, and thereby, the EUV light 21 is generated.

The EUV light collector mirror 8 reflects the generated EUV light 21 in the rightward direction in the drawing to collect the EUV light 21 to the IF (intermediate focusing point). The EUV light 21 reflected by the EUV light collector mirror 8 passes through the gate valve 10 and the filter 11 provided in the EUV light generation chamber 13. Then, the EUV light 21 collected to the IF (intermediate focusing point) is guided to the exposure equipment etc. via the transmission optics.

The EUV light source apparatus further includes the purge gas supply units 31 and 32, a purge gas introduction path 35 for guiding the purge gas ejected from the purge gas supply unit 31 to the surface of the window 6 at the inner side of the EUV light generation chamber 13, and a purge gas introduction path 36 for guiding the purge gas ejected from the purge gas supply unit 32 to the reflecting surface of the spherical concave mirror 47.

Further, in the EUV light generation chamber 13, a purge gas chamber 51, that surrounds the window 6, and a purge gas chamber 52, that surrounds the spherical concave mirror 47 and the spherical concave mirror adjusting mechanism 48, are arranged. The upper portion of the purge gas chamber 51 in the drawing is tapered cylinder-shaped, and at the top end thereof (upper side in the drawing), an opening 51*a* for allowing the laser beam 20 having been transmitted through the window 6 to pass through is provided. The lower portion of the purge gas chamber 52 in the drawing is tapered cylinder-shaped, and at the top end thereof (lower side in the drawing), an opening 52*a* for allowing the laser beam 20 transmitted through the window 6 and the laser beam 20 reflected by the spherical concave mirror 47 to pass through is provided.

According to the present embodiment, since the spherical concave mirror 47 serves to correct chromatic aberration of the concave lens 45 and the convex lens 46, it is possible to more effectively collect the laser beam 20 than when the parabolic concave mirror is used.

Next, an EUV light source apparatus according to a fourth embodiment of the present invention will be described.

Figure 8:
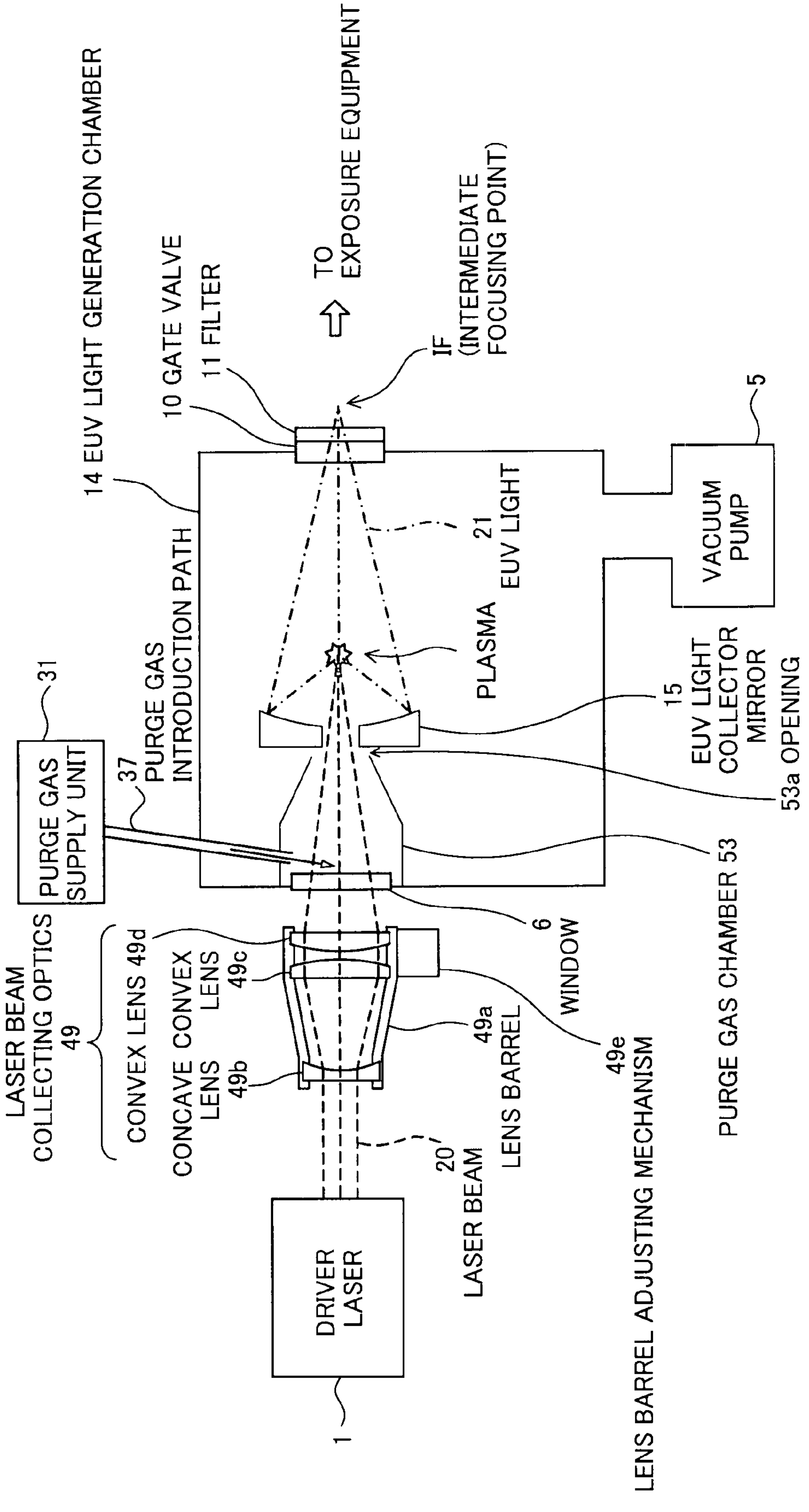
FIG. 8 is a schematic diagram showing an EUV light source apparatus according to a fourth embodiment of the present invention.

FIG. 8 is a schematic diagram showing the EUV light source apparatus according to the present embodiment. In FIG. 8, the target material supply unit 3 and the target material collection tube 7 (refer to FIG. 1) are not shown schematically, and it is assumed that the target material is ejected vertically to the drawing.

As shown in FIG. 8, the laser beam 20 emitted in the rightward direction in the drawing from the driver laser 1 enters a laser beam collecting optics 49.

The laser beam collecting optics 49 includes (i) a lens-barrel 49*a*, (ii) a concave lens 49*b*, convex lenses 49*c* and 49*d* arranged in the lens-barrel 49*a*, and (iii) a lens-barrel adjusting mechanism 49*e*. The laser beam 20 having entered the laser beam collecting optics 49 is enlarged by the concave lens 49*b*, collimated by the convex lens 49*c*, and collected by the convex lens 49*d*. The laser beam 20 collected by the convex lens 49*d* is transmitted through the window 6 and input into an EUV light generation chamber 14. The position and angle (tilt angle) of the lens-barrel 49*a* can be adjusted by the lens-barrel adjusting mechanism 49*e*.

In the EUV light generation chamber 14, an EUV light collector mirror 15, in the center of which a hole is formed, is arranged, and the laser beam 20 having entered the EUV light generation chamber 14 passes through the hole and is collected on an orbit of the target material. Due to this, the target material is excited and turned into plasma, and thereby, the EUV light 21 is generated.

The EUV light collector mirror 15 reflects the generated EUV light 21 in the rightward direction in the drawing to collect the EUV light 21 to the IF (intermediate focusing point). The EUV light 21 reflected by the EUV light collector mirror 15 passes through the gate valve 10 provided in the EUV light generation chamber 14 and the filter 11. The EUV light 21 collected to the IF (intermediate focusing point) is then guided to the exposure equipment or the like via the transmission optics.

The EUV light source apparatus further includes the purge gas supply unit 31, and a purge gas introduction path 37 for guiding the purge gas ejected from the purge gas supply unit 31 to the surface of the window 6 at the inner side of the EUV light generation chamber 14.

Further, to the inner wall of the EUV light generation chamber 14, a purge gas chamber 53 that surrounds the window 6 is attached. The right-hand part of the purge gas chamber 53 in the drawing is tapered cylinder-shaped, and at the top end thereof (on the right-hand side in the drawing), an opening 53*a* for allowing the laser beam 20 transmitted through the window 6 to pass through is provided.

Figure 9:
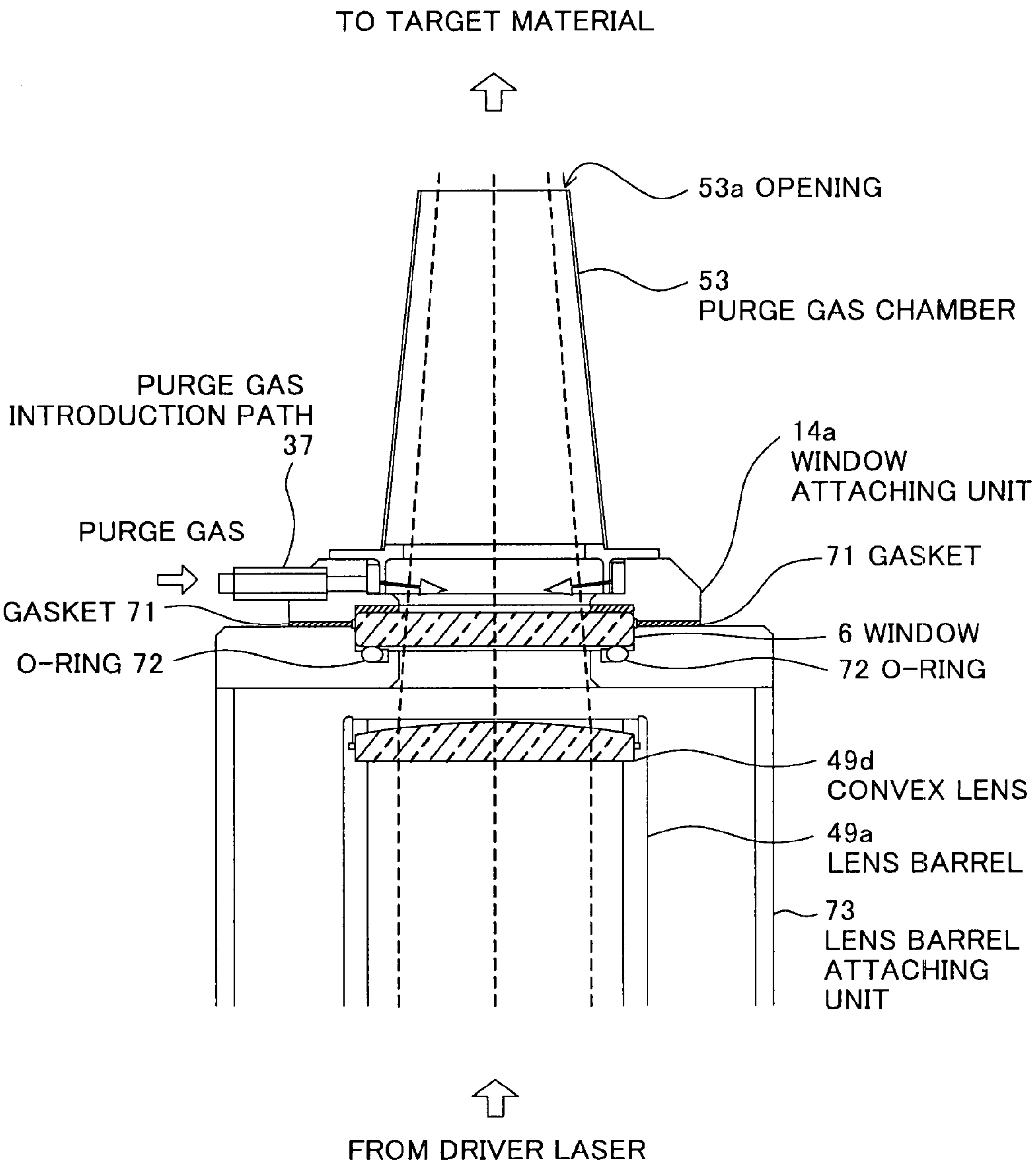
FIG. 9 is an enlarged diagram of the vicinity of a window in FIG. 8.
Figure 10:
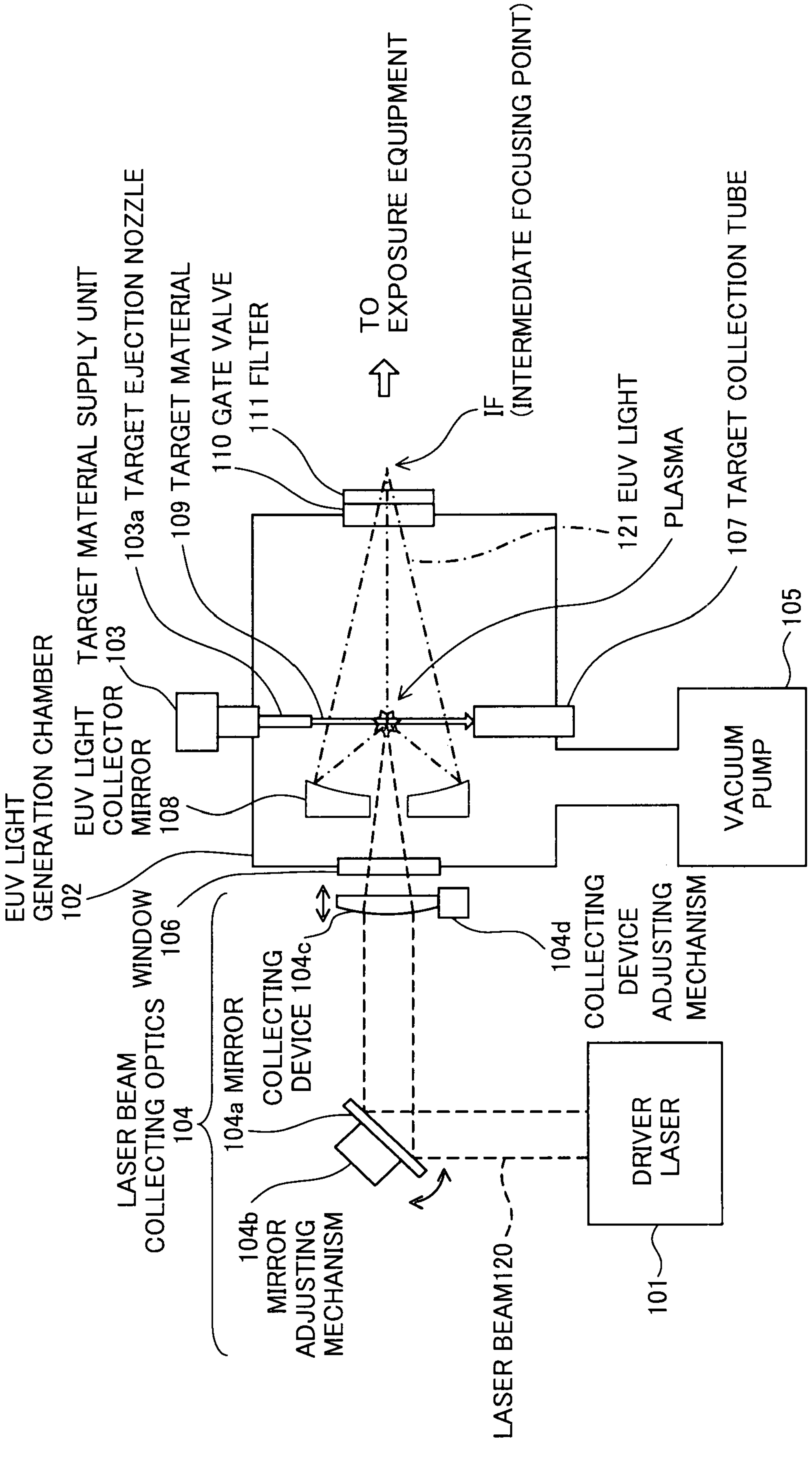
FIG. 10 is a schematic diagram showing an outline of a conventional EUV light source apparatus.

FIG. 9 is an enlarged view of the vicinity of the window 6 and the purge gas chamber 53. As shown in FIG. 9, the window 6 is attached between a window attaching unit 14*a* of the EUV light generation chamber 14 and a lens-barrel attaching unit 73 to which the lens-barrel 49*a* and the lens-barrel adjusting mechanism 49*e* are attached. Between the window attaching unit 14*a* and the window 6 and between the window attaching unit 14*a* and the lens-barrel attaching unit 73, a gasket 71 is arranged for sealing. In addition, between the window 6 and the lens-barrel attaching unit 73, an O-ring 72 is arranged. The window 6 is biased upward in the drawing by the O-ring 72. In the inner wall on the lower side of the purge gas chamber 53, a plurality of holes (for example, 12 holes) are formed and the purge gas supplied to the purge gas introduction path 37 is ejected toward the center of the upper surface of the window 6 in the drawing from the holes.

In the present embodiment, the three lenses (the concave lens 49*b*, and the convex lenses 49*c* and 49*d*) are used, however, four or more lenses may be used to reduce aberration.

The invention claimed is:

1. An extreme ultra violet light source apparatus which generates extreme ultra violet light by irradiating a target material with a laser beam and thereby turning said target material into plasma, said apparatus comprising:

- an extreme ultra violet light generation chamber in which extreme ultra violet light is generated;
- a target material supply unit which supplies a target material into said extreme ultra violet light generation chamber;
- a driver laser which generates a laser beam;
- a window which is provided in said extreme ultra violet light generation chamber and allows the laser beam to be transmitted into said extreme ultra violet light generation chamber, a surface of said window being disposed at an inner side of said extreme ultra violet light generation chamber;
- a laser beam collecting optical device which collects the laser beam generated by said driver laser to a target material supplied into said extreme ultra violet light generation chamber so as to generate plasma, said laser beam collecting optical device including an optical surface arranged in said extreme ultra violet light generation chamber;
- an extreme ultra violet light collecting optical device which collects the extreme ultra violet light generated from said plasma to output the extreme ultra violet light;
- a purge gas supply unit which supplies a purge gas for protecting at least one of (i) said surface of said window and (ii) said optical surface of said laser beam collecting optical device;
- a laser beam detector protection unit through which the laser beam passes after being collected by said laser beam collecting optical device;
- a laser beam image forming optics which forms an image of the laser beam collected by said laser beam collecting optical device;
- a laser beam detector which obtains information about a position at which the image of the laser beam is formed by said laser beam image forming optics; and
- an adjusting mechanism which carries out alignment of said laser beam collecting optical device based on the information obtained by said laser beam detector.

2. An extreme ultra violet light source apparatus according to claim 1, wherein said purge gas supply unit ejects the purge gas to at least one of (i) the surface of said window at the inner side of said extreme ultra violet light generation chamber and (ii) the optical surface of said at least one optical device arranged in said extreme ultra violet light generation chamber.

3. An extreme ultra violet light source apparatus according to claim 1, further comprising:

- at least one purge gas chamber arranged to surround at least one of (i) the surface of said window at the inner side of said extreme ultra violet light generation chamber and (ii) said at least one optical device arranged in said extreme ultra violet light generation chamber, said purge gas chamber having an opening which allows the laser beam to pass through.

4. An extreme ultra violet light source apparatus according to claim 1, wherein:

- said laser beam collecting optical device includes a plurality of optical devices; and
- said laser beam collecting optical device has a back focus a length which is longer than a focal length of one of said plurality of optical devices arranged at a light output side.

5. An extreme ultra violet light source apparatus according to claim 4, wherein said laser beam collecting optical device includes:

- a first lens which is arranged outside said extreme ultra violet light generation chamber and enlarges the laser beam generated by said driver laser;
- a second lens which is arranged outside said extreme ultra violet light generation chamber and collimates the laser beam enlarged by said first lens; and
- one of a parabolic concave mirror and a spherical concave mirror which is arranged inside said extreme ultra violet light generation chamber and reflects the laser beam collimated by said second lens to collect the laser beam onto a path of the target material in said extreme ultra violet light generation chamber.

6. An extreme ultra violet light source apparatus according to claim 4, wherein said laser beam collecting optical device includes:

- a first lens which is arranged outside said extreme ultra violet light generation chamber and enlarges the laser beam generated by said driver laser;
- a second lens which is arranged outside said extreme ultra violet light generation chamber and collimates the laser beam enlarged by said first lens; and
- a third lens which is arranged outside said extreme ultra violet light generation chamber and collects the laser beam collimated by said second lens onto an orbit of the target material in said extreme ultra violet light generation chamber.

7. An extreme ultra violet light source apparatus according to claim 1, wherein said laser beam collecting optical device includes:

(i) a first lens which is arranged outside said extreme ultra violet light generation chamber and enlarges the laser beam generated by said driver laser;

(ii) a second lens which is arranged outside said extreme ultra violet light generation chamber and collimates the laser beam enlarged by said first lens; and (iii) a concave mirror which is arranged inside said extreme ultra violet light generation chamber and reflects the laser beam collimated by said second lens to collect the laser beam onto a path of the target material in said extreme ultra violet light generation chamber, and wherein said purge gas supply unit is arranged to direct the purge gas at said concave mirror.

8. An extreme ultra violet light source apparatus according to claim 1, wherein said laser beam collecting optical device includes:

(i) a first lens which is arranged outside said extreme ultra violet light generation chamber and enlarges the laser beam generated by said driver laser;

(ii) a second lens which is arranged outside said extreme ultra violet light generation chamber and collimates the laser beam enlarged by said first lens; and (iii) a concave mirror which is arranged inside said extreme ultra violet light generation chamber and reflects the laser beam collimated by said second lens to collect the laser beam onto a path of the target material in said extreme ultra violet light generation chamber, wherein said purge gas supply unit is arranged to direct the purge gas at said concave mirror, and wherein an additional purge gas supply unit is arranged to direct purge gas at said surface of said window.

9. An extreme ultra violet light source apparatus which generates extreme ultra violet light by irradiating a target material with a laser beam and thereby turning said target material into plasma, said apparatus comprising:

an extreme ultra violet light generation chamber in which extreme ultra violet light is generated;

a target material supply unit which supplies a target material into said extreme ultra violet light generation chamber;

a driver laser which generates a laser beam;

a window which is provided in said extreme ultra violet light generation chamber and allows the laser beam to be transmitted into said extreme ultra violet light generation chamber;

a laser beam collecting optical device which collects the laser beam generated by said driver laser to a target material supplied into said extreme ultra violet light generation chamber so as to generate plasma;

an extreme ultra violet light collecting optical device which collects the extreme ultra violet light generated from said plasma to output the extreme ultra violet light;

a laser beam image forming optical device which forms an image of the laser beam collected by said laser beam collecting optical device;

a laser beam detector which obtains information about a position at which the image of the laser beam is formed by said laser beam image forming optical device; and an adjusting mechanism which carries out alignment of said laser beam collecting optical device based on the information obtained by said laser beam detector.

* * * * *